United States Patent
Teoh et al.

[11] Patent Number: 5,758,253
[45] Date of Patent: May 26, 1998

[54] SINTERED TITANIUM-GRAPHITE COMPOSITE AND METHOD OF MAKING

[75] Inventors: Swee Hin Teoh; Rajendran Thampuran; James Cho Hong Goh; Winston Kar Heng Seah, all of Singapore, Singapore

[73] Assignee: National University of Singapore, Singapore, Singapore

[21] Appl. No.: 726,732

[22] Filed: Oct. 7, 1996

[30] Foreign Application Priority Data

Oct. 7, 1995 [SG] Singapore ............... 9501510-3

[51] Int. Cl.$^6$ ............... B22F 3/12
[52] U.S. Cl. ............... 419/2; 419/11; 419/17; 419/26; 419/38; 419/39; 419/57; 419/45; 419/60; 75/231; 75/237; 75/245; 264/DIG. 36
[58] Field of Search ............... 419/2, 17, 11, 419/38, 39, 45, 57, 60, 26; 75/237, 245, 231; D34/155; 424/422, 423; 264/DIG. 36

[56] References Cited

U.S. PATENT DOCUMENTS

| | | | |
|---|---|---|---|
| 3,986,212 | 10/1976 | Sauer | 3/1.91 |
| 4,164,794 | 8/1979 | Spector et al. | 3/1.912 |
| 4,278,630 | 7/1981 | Scheicher | 264/60 |
| 4,601,874 | 7/1986 | Marty et al. | 419/23 |
| 4,659,546 | 4/1987 | Kearns | 419/2 |
| 4,923,513 | 5/1990 | Ducheyne | 75/245 |
| 4,931,253 | 6/1990 | Eylon et al. | 419/25 |
| 5,254,509 | 10/1993 | Gesing et al. | 501/93 |
| 5,256,368 | 10/1993 | Oden et al. | 419/10 |
| 5,278,109 | 1/1994 | Ono et al. | 501/87 |
| 5,336,465 | 8/1994 | Matsunaga et al. | 419/2 |
| 5,409,518 | 4/1995 | Saito et al. | 75/44 |
| 5,441,537 | 8/1995 | Kenna | 419/2 |
| 5,443,510 | 8/1995 | Shetty et al. | 419/2 |

*Primary Examiner*—Daniel J. Jenkins
*Attorney, Agent, or Firm*—Lowe, Price, LeBlanc & Becker

[57] ABSTRACT

A process for producing sintered titanium-graphite having improved wear resistance and low frictional characteristics is described. The said process which produces titanium-graphite composites having a triphasic structure with controlled porosity and a graphite lubricating film, comprises sintering a mixture of titanium and graphite powders in which the percentage of graphite may vary from 4 to 8 percent at temperatures from about 800° C. to 1600° C., for about ½ to 2 hours, under a compaction pressure of 0.17 to 0.62 MPa. The composites have applications in biomedical engineering and other fields of engineering due to their biocompatibility, strength and improved wear resistance.

6 Claims, 3 Drawing Sheets

SINTERED TITANIUM-GRAPHITE COMPOSITE AND METHOD OF MAKING

FIELD OF THE INVENTION

This invention relates to a sintered titanium-graphite composite having a triphasic structure, and more specifically, the invention relates to the powder metallurgy process for producing hard-wearing and low frictional characteristics composites having structures that can be porous and with a graphite lubricating film suitable in biomedical and other industrial applications.

BACKGROUND OF THE INVENTION

In many applications notably, subspace, supersonic flight, refractory materials and biomaterials, new concepts in materials processing are required to develop materials designed to function under optimum conditions of temperature, loading and adverse environment. Traditional materials like aluminum and its alloys, titanium and its alloys and steels do have some of the necessary combination of high strength, temperature resistance and high modulus but often require further processing to enhance certain properties such as nitriding on the surface of titanium to improve wear performance. The traditional methods are often expensive and require laborious work to develop the required material properties.

One of the main advantages of powder metallurgy is the low cost needed to fabricate materials. The technology is old but has found use in the applications like oil impregnated-porous bronze bearings. There are two ways in which alloys may be fabricated powder metallurgically, the first, is by sintering powders of the alloys where the final product has often been found to provide significant cost saving compared to other methods and the second, by sintering two or more different powders where control of the sintering process restricts the interdiffusion between the powders and the final product is customised to specific needs.

The kinetics and other aspects of sintering binary powders have been elucidated by many researchers where the objective is essentially to achieve a perfect state of homogenisation between the powders and any element is not left discretized from the bulk. For example, in iron-nickel systems the aim has been to fabricate a homogenous material of iron and nickel as opposed to a precipitated presence of nickel in iron.

Powders of titanium, titanium carbide or graphite in combination with each other have been studied previously but not in the production of a triphase composite. These attempts have generally been to understand the stoichiometric nature of diffusion between these materials. For example, pure titanium and graphite powders have been used with the aim of evaluating the stoichiometric proportions that would lead to complete homogenisation resulting in the fabrication of titanium carbide. Titanium carbide is a well known refractory material with excellent wear properties [6] and attempts such as those cited above have been dedicated to developing this ceramic powder metallurgically.

However, in certain application like in biomaterials, the requirement is a composite that will have phases which maintain the biocompatibility, mechanical strength and still have good wear resistance and frictional properties. Examples of prior art that have been patented where sintered materials have been specifically designed to improve the mechanical strength and abrasion resistance include patents by Kinzoku (JP 55-18508) and Gijutsu and Honbu (JP 56-25946).

If powders of different types were used, the compacts formed due to the material transport of the various powders result in a powder metallurgical system that has different phases. Mixed powders have been in use for many years (German RM., Powder Metallurgical Science, Metal Powder Industries Federation, Princeton, N.Y., 1984) mostly in the development of improved cutting tools.

The main advantage is that components that have "tailor-made" properties can be fabricated.

OBJECT OF THE INVENTION

It is a primary object of this invention to provide a powder metallurgy process for producing sintered titanium—titanium carbide—graphite composites having the various degrees of porosity and wear resistance as desired.

It is another object of this invention to provide a porous, hard-wearing and biocompatible material for use in prostheses in biomedical engineering applications. It is a further object of the invention to provide a titanium-graphite composite whose density, strength, and wear properties may be tailored to other industrial applications.

Other objects, features and advantages of the invention will become apparent from the detailed description which follows, or may be learned from the practice of the invention.

SUMMARY OF THE INVENTION

The development of a wear resistant titanium composite can be achieved by sintering pure titanium and graphite powders. In this system, control of the sintering process enables a triphasic composite to be fabricated that include elements of pure titanium that provides bulk mechanical strength, titanium carbide that provides a hard wear resistance phase and free graphite that has well known lubricating qualities that further enhances the wear resistance and frictional properties of a composite.

DESCRIPTION OF THE EMBODIMENTS OF THE INVENTION

Figure 1:
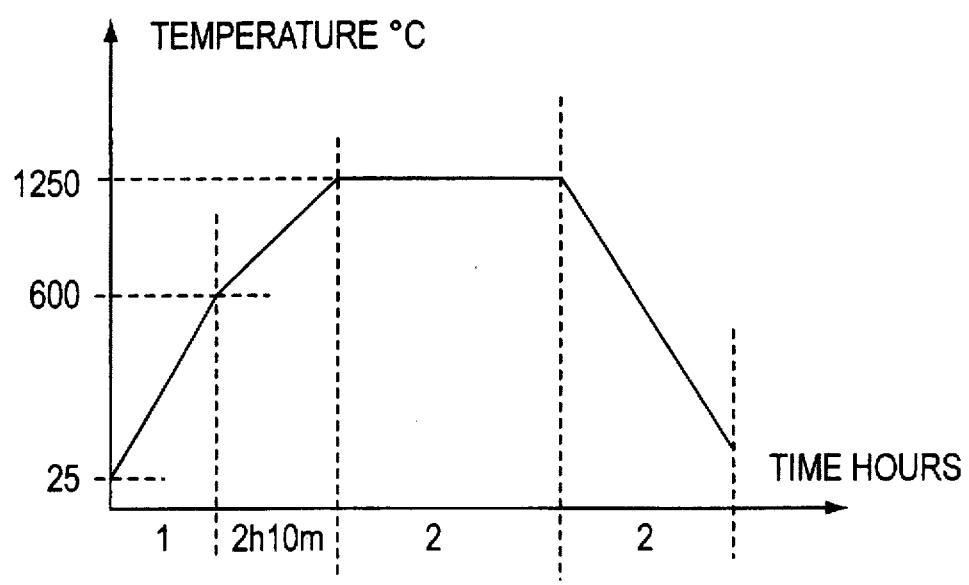
FIG. 1 shows a typical heating cycle of the sintering process.

In this invention pure titanium and graphite powders were mixed, compacted and sintered under the process conditions described below to produce a range of triphasic titanium-graphite composites with high wear resistance and low frictional characteristics.

Graphite is an allotrope of carbon which has well known lubricating properties. The rationale for the use of graphite was to produce a hard, wear resistant titanium carbide phase. By controlling the sintered temperature, carbon atoms migrate to titanium and form titanium carbide. Whilst titanium carbide is a hard material, it has poor mechanical properties in terms of fracture and tensile strength. For this reason, it is beneficial to maintain pure titanium as the bulk element. To achieve this objective, complete dissolution of carbon atoms is prevented by controlling the processing method.

In biomedical applications such as hip and knee prostheses, it is often beneficial to maintain a porous structure that allows for osseointegration. The sintered compacts developed and described in the following sections have inherent pores to simulate the typical requirements such as those in orthopaedic biomaterials.

Powder selection

Commercially available pure titanium and graphite were used as the component powders. The nominal elements found in the powders are shown in Table 1 (a) and (b). The mean particle size of the pure titanium powders was 150 μm and the particle shape was irregular, flaky or ligamental. Graphite powders had a mean particle size of 100 μm with irregular and ligamental shapes.

Compacts with compositions of 8% and 4% by weight of graphite were produced. This was done by blending powders with a total weight of 10g. Variations in powder weight were less than 0.005 g. The 10 g portions of titanium and graphite powders were blended in a Y-Cone blender at 30 rpm for 1 hour to ensure that the powders were well mixed.

TABLE 1(a)

Typical composition of trace elements in pure titanium powder

| Elements | Composition (ppm) of traces of Titanium |
|---|---|
| iron | 0.2 |
| aluminum | 0.2 |
| manganese | 0.3 |
| chromium | 0.2 |

TABLE 1(b)

Typical composition of trace elements in pure graphite powder

| Elements | Composition (ppm) of traces of Graphite |
|---|---|
| aluminum | 0.2 |
| iron | 0.2 |
| manganese | 0.3 |
| silicon | 0.2 |

Compaction

Various mixed powders of 8% and 4% graphite were compacted to four different compaction pressures namely, 5, 10, 14 and 18 tons. Compaction was performed in a punch-die set on a hydraulic press. Compaction was carried out in gradual steps of 2, 5, 8, 10, 12, 14, 16 and 18 tons to assist in particle relocation and rearrangement.

Studies on the compaction behaviour of graphite-titanium mixed powders showed that the maximum allowable graphite composition prior to fracture during compaction was around 8%. The second series of compacts with 4% was chosen to assess the influence of graphite on the wear resistance of these composites.

Sintering

Sintering was performed in a vacuum oven (carbolite) at $10^{-6}$ mbars. The compacts were placed in a ceramic tube (=10 cm in length) and the ends were encased in a stainless steel foil to prevent contamination from elements inside the oven.

Sintering was performed at 1250° C. for 2 hours. The heating cycle was performed as shown in FIG. 1. There were four stages to the heating cycle. The furnace was initially heated at a rate of 10° C./min up to 600° C., and then heated at 5° C./min up to 1250° C. The temperature was then maintained at 1250° C. for 2 hours before cooling at a rate of 10° C./min to room temperature. This heating cycle prevents phase changes occurring in different regimes of heating rates and also overshooting of the maximum temperature.

Sintering at temperatures that range from 800° C. to 1600° C. for duration of more than 30 minutes may also be used to produce the desired composite.

The environment during sintering may be a vacuum or any other inert condition such that oxidation of the titanium does not take place during the diffusion of titanium and graphite.

After sintering, the compacts were deburred and weight cum height measurements were taken to evaluate the density of the compacts as follows:

$$\text{Density of the compact} = \frac{\text{Weight of compact}}{\text{Volume of compact}}$$

$$\text{Relative Density} = \frac{\text{Density of compacts}}{\text{Relative density of the composite}}$$

Relative density is evaluated from the rule of mixtures which is the sum of the densities, by weight, of the two components. The densities of the 8% and 4% compacts are given in Tables 2(a) and (b).

TABLE 2(a)

Density and Pore Size of the Ti-8% Graphite Composite

| Pressure of Compaction (tons/GPa) | Density (%) | Pore Size (μm) |
|---|---|---|
| 5/0.17 | 66 | 110 |
| 10/0.34 | 79 | 71 |
| 14/0.48 | 84 | 60 |
| 18/0.62 | 88 | 55 |

TABLE 2(b)

Density and Pore Size of the Ti-4% Graphite Composite

| Pressure of Compaction (tons/GPa) | Density (%) | Pore Size (μm) |
|---|---|---|
| 5/0.17 | 62 | 120 |
| 10/0.34 | 73 | 80 |
| 14/0.48 | 80 | 60 |
| 18/0.62 | 84 | 60 |

The pores in the 5 ton compacts were large and interconnected. The pores became smaller and more isolated with increasing densification. Numerous compacts were fabricated using the above mentioned technique and the pore size and densities did not vary by more than 5%.

Wear resistance of the composites

A marked improvement in the wear resistance of the titanium-graphite system has been demonstrated by comparing the wear rates with those of pure titanium compacts under the same compaction pressures and sintering regimes. The wear tests were performed on a pin-on-disc test rig with a load of 50N and a sliding speed of 0.2 m/s.

Figure 2A:
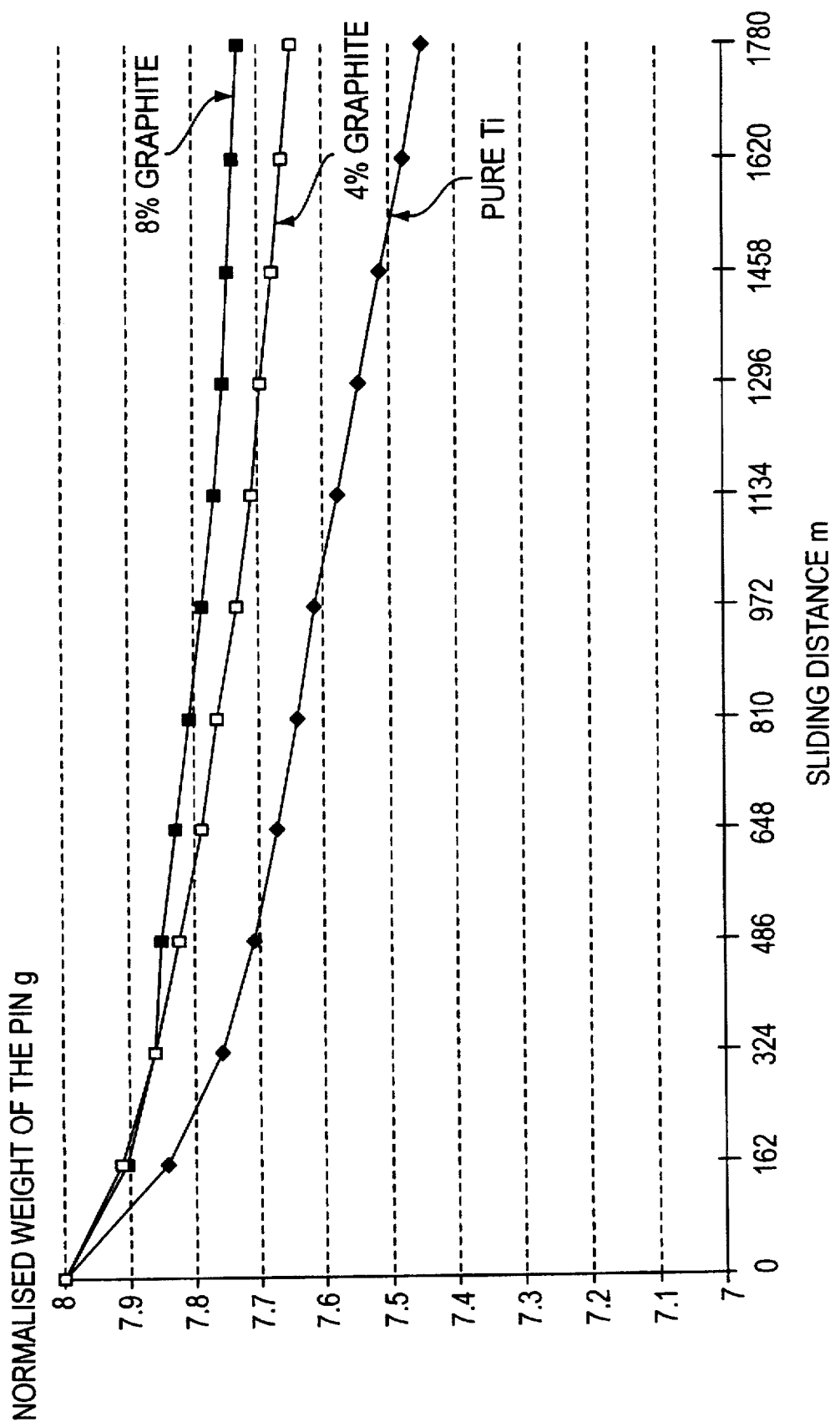
FIG. 2a shows the wear performance of the composite as compared to pure sintered titanium.
Figure 2B:
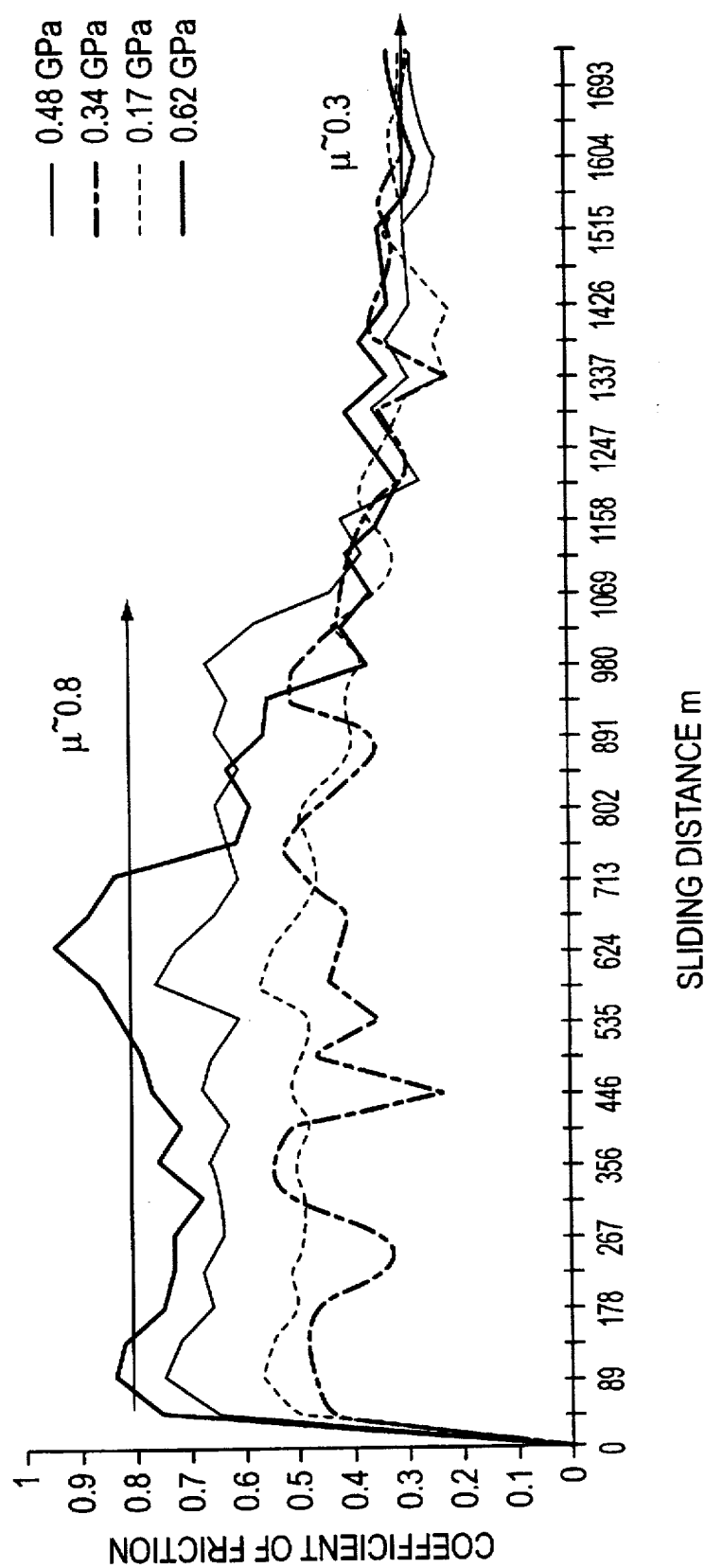
FIG. 2b shows the coefficient of friction of the various 8% graphite composites.

With compacts of 4% graphite, wear improvements of up to 1.5 times have been observed. An increase in wear resistance of up to 2.5 times can be demonstrated by increasing the composition of graphite to 8%. This is attributed to the presence of a hard titanium carbide phase that is supplemented by a lubricating sacrificial film of pure graphite. In addition, the lubricating graphite film reduced the coefficient of friction. FIG. 2 (a) and (b) show the typical improvements in wear and friction of the composites.

We claim:

1. A process for producing a powder metallurgy composite with three phases including pure titanium, titanium carbide and free graphite comprising the steps of:

sintering a mixture of titanium and graphite powders at about 800° C. to about 1600° C. for about 0.5 to about 2 hours wherein the percentage of graphite varies from about 4 to about 8 percent.

2. The process of claim 1, wherein the sintering process is carried out in vacuum.

3. The process of claim 1 wherein the sintering process is carried out in an inert atmosphere.

4. A titanium—titanium carbide—graphite composite produced under the process in claim 1.

5. A method for producing an orthopaedic or other biomaterial comprising the step of providing the composite of claim 4 and forming said composite into an orthopaedic or other biomaterial.

6. A biomaterial comprising the composite of claim 4 which is wear resistant with lubricating properties.

* * * * *